(12) United States Patent
Rodgers et al.

(10) Patent No.: US 12,356,949 B2
(45) Date of Patent: *Jul. 15, 2025

(54) ANTHRACNOSE RESISTANT ALFALFA PLANTS

(71) Applicant: Forage Genetics International, LLC, West Salem, WI (US)

(72) Inventors: Charles A. Rodgers, Onalaska, WI (US); Mark H. McCaslin, Shoreview, MN (US); David D. Witte, West Salem, WI (US); Julie Chiu-Lee Ho, Davis, CA (US); John Nicholas Cameron, Woodland, CA (US)

(73) Assignee: Forage Genetics International, LLC, West Salem, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/480,748

(22) Filed: Oct. 4, 2023

(65) Prior Publication Data

US 2024/0099256 A1   Mar. 28, 2024

Related U.S. Application Data

(63) Continuation of application No. 17/353,488, filed on Jun. 21, 2021, now Pat. No. 11,800,848, which is a continuation of application No. 16/035,133, filed on Jul. 13, 2018, now Pat. No. 11,051,482.

(60) Provisional application No. 62/532,151, filed on Jul. 13, 2017.

(51) Int. Cl.
   *A01H 5/10* (2018.01)
   *A01H 5/12* (2018.01)
   *A01H 6/54* (2018.01)
   *C12Q 1/6895* (2018.01)

(52) U.S. Cl.
   CPC .............. *A01H 6/544* (2018.05); *A01H 5/10* (2013.01); *A01H 5/12* (2013.01); *C12Q 1/6895* (2013.01); *C12Q 2600/13* (2013.01); *C12Q 2600/156* (2013.01)

(58) Field of Classification Search
   None
   See application file for complete search history.

(56) References Cited

U.S. PATENT DOCUMENTS

| | | | |
|---|---|---|---|
| 7,968,769 B2 | 6/2011 | Velde | |
| 8,138,392 B2 | 3/2012 | Uppalapati et al. | |
| 9,139,848 B2 | 9/2015 | Velde | |
| 9,701,976 B2 | 7/2017 | Levering et al. | |
| 11,051,482 B2* | 7/2021 | Rodgers | A01H 5/12 |
| 11,800,848 B2* | 10/2023 | Rodgers | A01H 5/12 |
| 2008/0050821 A1 | 2/2008 | Johnson et al. | |
| 2008/0263723 A1 | 10/2008 | Velde | |
| 2015/0052636 A1 | 2/2015 | Hartig et al. | |

OTHER PUBLICATIONS

Declaration of Julie Ho, PH.D. Under 37 C.F.R. § 1.132 regarding U.S. Appl. No. 16/035,133, dated Jun. 17, 2020.
A Report of the Alfalfa and Miscellaneous Legumes Variety Review Board; AOSCA, Jan. 2017.
NAFA, Alfalfa Variety Ratings, 2015.
International Search Report and Opinion Regarding International Application No. PCT/US18/42072, dated Sep. 28, 2018.
Rodgers, "Breeding Resistance to New Races of Anthracnose," Joint Conference NAAIC, Trifolium and Grass Breeders, 2016.
Supplementary European Search Report regarding European App. No. 18831855.4, dated Feb. 22, 2021.
Saunders et al., The characterization of defense responses to fungal infection in alfalfa, BioControl 49(6):715-728, 2004.
Yang et al., Genetic and physical localization of an anthracnose resistance gene in Medicago truncatula, Theoretical and Applied Genetics 116(1):45-52, 2007.

* cited by examiner

*Primary Examiner* — Medina A Ibrahim
(74) *Attorney, Agent, or Firm* — Dentons US LLP

(57) ABSTRACT

The present disclosure provides alfalfa plants exhibiting broad spectrum resistance to Race 1, Race 2, and Race 5 anthracnose. Such plants may comprise novel introgressed genomic regions associated with disease resistance from Race 1, Race 2, and Race 5 anthracnose. In certain aspects, compositions, including novel polymorphic markers and methods for producing, breeding, identifying, and selecting plants or germplasm with a disease resistance phenotype are provided. Also provided are alfalfa varieties designated as C0416C4164 and H0415C4114. Provided by the invention are the seeds, plants and derivatives of alfalfa varieties C0416C4164 and H0415C4114. Also provided by the invention are tissue cultures of alfalfa varieties C0416C4164 and H0415C4114, and the plants regenerated therefrom. Still further provided by the invention are methods for producing alfalfa plants by crossing alfalfa variety C0416C4164 or H0415C4114 with itself or another alfalfa variety and plants produced by such methods.

7 Claims, 4 Drawing Sheets
Specification includes a Sequence Listing.

ANTHRACNOSE RESISTANT ALFALFA PLANTS

REFERENCE TO RELATED APPLICATIONS

This application is a continuation of U.S. patent application Ser. No. 17/353,488, filed Jun. 21, 2021, which is a continuation of U.S. patent application Ser. No. 16/035,133, filed Jul. 13, 2018, now U.S. Pat. No. 11,051,482, which claims the benefit of U.S. Provisional Application No. 62/532,151, filed Jul. 13, 2017, each of which is herein incorporated by reference in its entirety.

INCORPORATION OF SEQUENCE LISTING

A sequence listing containing the file named "LLKS004USC2_ST26.xml" which is 9.8013.5 kilobytes (measured in MS-Windows®) and created on Sep. 20, 2023, and comprises 7 sequences, is incorporated herein by reference in its entirety.

FIELD OF THE INVENTION

The present invention relates to the field of agriculture and more specifically to methods and compositions for producing alfalfa plants exhibiting improved resistance to anthracnose (*Colletotrichum trifolii*).

BACKGROUND OF THE INVENTION

Disease resistance is an important trait in agriculture, particularly in a crop such as alfalfa. Alfalfa can be grown in wide range of climates and ecosystems and is one of the United States most valuable food-production related crops. Anthracnose in alfalfa plants, caused by *Colletotrichum trifolii*, is one of the most serious diseases affecting alfalfa and results in stem death, crown rot, and reduced winter survival. Alfalfa resistant to one race of anthracnose may not be resistant to another race of anthracnose. New alfalfa lines comprising resistance to one or more races of anthracnose are needed given the significant importance of this disease in crop production.

SUMMARY OF THE INVENTION

One aspect of the invention provides a *Medicago sativa* plant comprising an introgressed allele conferring to said plant increased broad-spectrum resistance to *Colletotrichum trifolii* Race 5 compared with a plant not comprising said allele, wherein a representative sample of seed comprising said allele has been deposited under ATCC Accession No. PTA-124210 or under ATCC Accession No. PTA-125043. In some aspects, the allele is partially dominant. In other aspects, the introgressed allele comprises the resistance haplotype found in H0415C4112, H0415C4114, H0415C4115, or H0415C4116. The invention also relates to anthracnose resistant *Medicago sativa* plants, wherein the broad-spectrum resistance to *Colletotrichum trifolii* confers resistance to *Colletotrichum trifolii* Races 1, 2, and 5. The invention also relates to anthracnose resistant *Medicago sativa* plants, wherein said broad-spectrum resistance to *Colletotrichum trifolii* confers resistance to *Colletotrichum trifolii* Race 5. Further provided are seeds that produce a *Medicago sativa* plant comprising an introgressed allele conferring to said plant increased broad-spectrum resistance to *Colletotrichum trifolii* Race 5 compared with a plant not comprising said allele wherein a representative sample of seed comprising said allele has been deposited under ATCC Accession No. PTA-124210 or under ATCC Accession No. PTA-125043. Further provided are plant parts, including cells, seeds, roots, stems, leaves, heads, flowers, or pollen. Also provided are progeny plants of the *Medicago sativa* plants described herein.

Another aspect of the invention provides method for producing a *Medicago sativa* plant with broad-spectrum resistance to *Colletotrichum trifolii*, comprising the steps of: a) crossing the plant of claim 1 with itself or with a *Medicago sativa* plant of a different genotype to produce one or more progeny plants; and b) selecting a progeny plant comprising said allele. In further aspects, the selecting said progeny plant comprises identifying a genetic marker genetically linked to said allele. In other aspects of the method, the selecting a progeny plant comprises identifying a genetic marker within or genetically linked to a genomic region flanked in the genome of said plant by first identified marker locus and second identified marker locus. In yet further aspects of the method, the selecting a progeny plant comprises detecting at least one polymorphism at a locus selected from the group consisting of first marker locus, second marker locus, and third marker locus. In other aspects of the method, the progeny plant is an F2-F6 progeny plant. In further aspects of the method, the producing said progeny plant comprises backcrossing. In other aspects of the method, backcrossing comprises from 2-7 generations of backcrossing. In yet another aspect, the method provides a plant produced by the method.

The invention also relates to a plant of alfalfa variety C0416C4164, representative seed of said alfalfa variety having been deposited under ATCC Accession No. PTA-124210. Also provided is a plant part of the plant of alfalfa variety C0416C4164, wherein the plant part comprises at least one cell of said plant.

In a further aspect, provided is a seed of alfalfa variety C0416C4164, wherein representative seed of said alfalfa variety have been deposited under ATCC Accession No. PTA-124210. Also provided is a method of producing alfalfa seed, the method comprising crossing the plant of the seed of alfalfa variety C0416C4164, wherein representative seed of said alfalfa variety have been deposited under ATCC Accession No. PTA-124210, with itself or a second alfalfa plant to produce said alfalfa seed. In further aspects, the method further comprising crossing the plant of alfalfa variety C0416C4164 with a second, nonisogenic alfalfa plant to produce said alfalfa seed. In yet further aspect, an $F_1$ alfalfa seed produced by the method of producing alfalfa seed. Also provided is an alfalfa plant produced by growing the $F_1$ alfalfa seed.

Another aspect of the invention relates to a composition comprising the seed of alfalfa variety C0416C4164, wherein representative seed of said alfalfa variety have been deposited under ATCC Accession No. PTA-124210, further comprised in plant seed growth media. In further aspects, the plant seed growth media is soil or a synthetic cultivation medium.

In a further aspect, provided is a method of producing alfalfa seed, the method comprising crossing the plant of the seed of alfalfa variety C0416C4164, wherein representative seed of said alfalfa variety have been deposited under ATCC Accession No. PTA-124210, with itself or a second alfalfa plant to produce said alfalfa seed, wherein the method further comprising: (a) crossing a plant grown from said alfalfa seed with itself or a different alfalfa plant to produce seed of a progeny plant of a subsequent generation; (b) growing a progeny plant of a subsequent generation from said seed of a progeny plant of a subsequent generation and crossing the progeny plant of a subsequent generation with itself or a second plant to produce seed of a progeny plant of a further subsequent generation; and (c) repeating step (b) with sufficient inbreeding to produce seed of an inbred alfalfa plant that is derived from alfalfa variety C0416C4164. In other aspects, the method further comprises crossing a plant grown from said seed of an inbred alfalfa plant that is derived from alfalfa variety C0416C4164 with a nonisogenic plant to produce seed of a hybrid alfalfa plant that is derived from alfalfa variety C0416C4164.

The invention also relates to a method of producing a commodity plant product, the method comprising producing the commodity plant product from a plant of alfalfa variety C0416C4164, representative seed of said alfalfa variety having been deposited under ATCC Accession No. PTA-124210. In further aspects, the method produces a commodity plant product, wherein the commodity plant product comprises at least one cell of alfalfa variety C0416C4164.

The invention also relates to a plant of alfalfa variety H0415C4114, representative seed of said alfalfa variety having been deposited under ATCC Accession No. PTA-125043. Also provided is a plant part of the plant of alfalfa variety H0415C4114, wherein the plant part comprises at least one cell of said plant.

In a further aspect, provided is a seed of alfalfa variety H0415C4114, wherein representative seed of said alfalfa variety have been deposited under ATCC Accession No. PTA-125043. Also provided is a method of producing alfalfa seed, the method comprising crossing the plant of the seed of alfalfa variety H0415C4114, wherein representative seed of said alfalfa variety have been deposited under ATCC Accession No. PTA-125043, with itself or a second alfalfa plant to produce said alfalfa seed. In further aspects, the method further comprising crossing the plant of alfalfa variety H0415C4114 with a second, nonisogenic alfalfa plant to produce said alfalfa seed. In yet further aspect, an $F_1$ alfalfa seed produced by the method of producing alfalfa seed. Also provided is an alfalfa plant produced by growing the $F_1$ alfalfa seed.

Another aspect of the invention relates to a composition comprising the seed of alfalfa variety H0415C4114, wherein representative seed of said alfalfa variety have been deposited under ATCC Accession No. PTA-125043, further comprised in plant seed growth media. In further aspects, the plant seed growth media is soil or a synthetic cultivation medium.

In a further aspect, provided is a method of producing alfalfa seed, the method comprising crossing the plant of the seed of alfalfa variety H0415C4114, wherein representative seed of said alfalfa variety have been deposited under ATCC Accession No. PTA-125043, with itself or a second alfalfa plant to produce said alfalfa seed, wherein the method further comprising: (a) crossing a plant grown from said alfalfa seed with itself or a different alfalfa plant to produce seed of a progeny plant of a subsequent generation; (b) growing a progeny plant of a subsequent generation from said seed of a progeny plant of a subsequent generation and crossing the progeny plant of a subsequent generation with itself or a second plant to produce seed of a progeny plant of a further subsequent generation; and (c) repeating step (b) with sufficient inbreeding to produce seed of an inbred alfalfa plant that is derived from alfalfa variety H0415C4114. In other aspects, the method further comprises crossing a plant grown from said seed of an inbred alfalfa plant that is derived from alfalfa variety H0415C4114 with a nonisogenic plant to produce seed of a hybrid alfalfa plant that is derived from alfalfa variety H0415C4114.

The invention also relates to a method of producing a commodity plant product, the method comprising producing the commodity plant product from a plant of alfalfa variety H0415C4114, representative seed of said alfalfa variety having been deposited under ATCC Accession No. PTA-125043. In further aspects, the method produces a commodity plant product, wherein the commodity plant product comprises at least one cell of alfalfa variety H0415C4114.

Another aspect of the invention also relates to a *Medicago sativa* plant comprising a recombinant chromosomal segment on chromosome 4, wherein said chromosomal segment comprises an introgressed *Colletotrichum trifolii* race 5 resistance allele conferring to said plant increased resistance to *Colletotrichum trifolii* race 5 compared to a plant not comprising said allele. In some aspects, the *Colletotrichum trifolii* race 5 resistance allele is located within a chromosomal segment is flanked by marker locus FG2208 (SEQ ID NO: 1) and marker locus FG27271 (SEQ ID NO: 7) on chromosome 4 in said plant. In other aspects, the recombinant chromosomal segment comprises a marker locus selected from the group consisting of FG2208 (SEQ ID NO: 1), FG2218 (SEQ ID NO: 2), FG27062 (SEQ ID NO: 3), FG2226 (SEQ ID NO: 4), FG27232 (SEQ ID NO: 5), FG27251 (SEQ ID NO: 6), and FG27271 (SEQ ID NO: 7) on chromosome 4. In other aspects the *Colletotrichum trifolii* race 5 resistance allele is located within a chromosomal segment in the genome of said plant flanked by 16,945,124 bp to 19,292,176 bp on the *Medicago truncatula* Mt4.0 map. In yet a further aspect, a sample of seed comprising said introgressed *Colletotrichum trifolii* race 5 resistance allele was deposited under ATCC Accession No. PTA-124210 or under ATCC Accession No. PTA-125043.

Another aspect of the invention relates to a method for producing a *Medicago sativa* plant with broad-spectrum resistance to *Colletotrichum trifolii*, comprising the steps of: a) crossing a *Medicago sativa* plant comprising a recombinant chromosomal segment on chromosome 4, wherein said chromosomal segment comprises an introgressed *Colletotrichum trifolii* race 5 resistance allele conferring to said plant increased resistance to *Colletotrichum trifolii* race 5 compared to a plant not comprising said allele, with itself or with a *Medicago sativa* plant of a different genotype to produce one or more progeny plants; and b) selecting a progeny plant comprising said allele. In one aspect, the selecting a progeny plant comprises detecting said allele flanked by marker locus FG2208 (SEQ ID NO: 1) and marker locus FG27271 (SEQ ID NO: 7). In another aspect, the progeny plant is an $F_2$-$F_6$ progeny plant. In a further aspect, the producing said progeny plant comprises backcrossing.

The invention also relates to a method of producing a *Medicago sativa* plant exhibiting resistance to *Colletotrichum trifolii* race 5, comprising introgressing into a plant a *Colletotrichum trifolii* race 5 resistance allele within a recombinant chromosomal segment flanked in the genome of said plant by marker locus FG2208 (SEQ ID NO: 1) and marker locus FG27271 (SEQ ID NO: 7) on chromosome 4, wherein said allele confers increased resistance to *Colletotrichum trifolii* race 5 compared to a plant not comprising said allele. In one aspect, the recombinant chromosomal segment comprises a marker locus selected from the group consisting of FG2208 (SEQ ID NO: 1), FG2218 (SEQ ID NO: 2), FG27062 (SEQ ID NO: 3), FG2226 (SEQ ID NO: 4), FG27232 (SEQ ID NO: 5), FG27251 (SEQ ID NO: 6), and FG27271 (SEQ ID NO: 7). In another aspect, said introgressing comprises backcrossing. In a further aspect, said introgressing comprises marker-assisted selection. In another aspect, said introgressing comprises assaying said plant for increased *Colletotrichum trifolii* race 5 resistance. In yet another aspect, the invention provides a *Medicago sativa* obtainable by the methods discloses herein.

DETAILED DESCRIPTION

Figure 1:
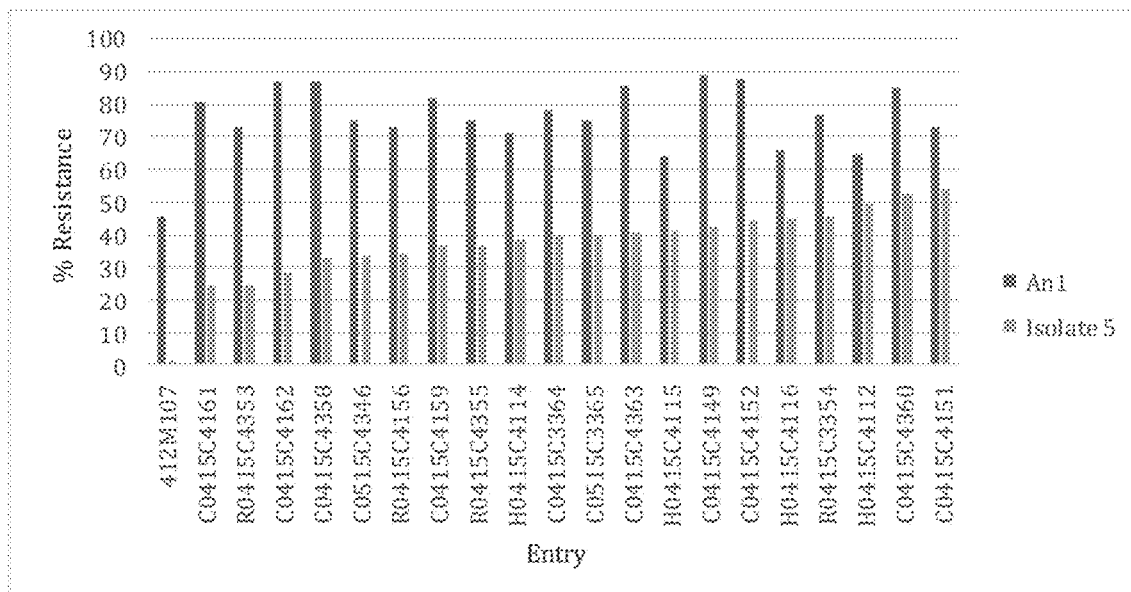
FIG. 1: Illustrates anthracnose race 5 resistance ratings for experimental varieties that were developed for race 5 anthracnose resistance.

Anthracnose (*Colletrotrium trifolii*) was first identified as an important alfalfa pathogen in the mid-late 1960's in the mid-Atlantic region of the U.S. Over the next decade anthracnose became one of the most damaging diseases in alfalfa over the entire eastern half of the country. An intensive breeding program at USDA Beltsville resulted in the commercial release of the anthracnose resistant variety Arc in 1974. By 1979 a new race of anthracnose had developed that overwhelmed the resistance gene An1 found in Arc. Although additional sources of resistance to anthracnose were subsequently developed, the rapid emergence of new races has made this disease a continued cause of significant crop loss. The present invention represents a significant advance in that it provides alfalfa plants resistant to newly identified Race 5 anthracnose, as well as Race 1 and Race 2.

I. Genomic Regions, Alleles, and Polymorphisms Associated With Anthracnose Resistance in Alfalfa Plants Anthracnose is a harmful alfalfa pathogen that typically kills or seriously injures alfalfa plants, such that infection with anthracnose can significantly and deleteriously impact crop yield of the plant. It is therefore desirable to identify specific genomic regions conferring resistance to specific races of anthracnose or broad-spectrum resistance to several races. Although intensive efforts to develop such resistance have been undertaken, previous efforts to develop new anthracnose resistant lines have met with limited success due to complicating factors such as linkage drag resulting in resistant lines with unacceptable agronomic quality. Further, in view of the emergence of new anthracnose races, new and durable resistance alleles are needed. Despite these obstacles, the present inventors have identified new sources of broad-spectrum anthracnose resistance and developed novel plant varieties comprising these resistance alleles.

The invention provides novel plant varieties along with novel introgressions of one or more alleles associated with increased anthracnose race 5 resistance in alfalfa plants, together with polymorphic nucleic acids and linked markers for tracking the introgressions during plant breeding. The novel plant varieties may be used together with the novel trait-linked markers provided herein in accordance with certain embodiments of the invention. In certain embodiments, the invention provides alfalfa plants comprising donor DNA from an anthracnose race 5 resistant line between marker locus FG2208 (SEQ ID NO: 1) and FG27271 (SEQ ID NO: 7) on chromosome 4.

One of skill in the art will understand that interval values may vary based on factors such as the reference map that is used, the sequencing coverage and the assembly software settings. However, such parameters and mapping protocols are known in the art and one of skill in the art can use the marker sequences provided herein to physically and genetically anchor the introgressions described herein to any given map using such methodology. The novel introgression of the present invention confers unique significantly improved agronomic properties over previously disclosed anthracnose resistance introgressions.

II. Introgression of Genomic Regions Associated with Disease Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel markers for identifying and tracking introgression of one or more of the genomic regions from an alfalfa into cultivated alfalfa lines. The invention further provides markers for identifying and tracking the novel introgressions disclosed herein during plant breeding, including markers relevant for identifying alfalfa plants with the desired Race 5 anthracnose resistance trait.

Markers within or linked to any of the genomic intervals of the present invention can be used in a variety of breeding efforts that include introgression of genomic regions associated with disease resistance into a desired genetic background. For example, a marker within 20 cM, 15 cM, 10 cM, 5 cM, 2 cM, or 1 cM of a marker associated with disease resistance described herein can be used for marker-assisted introgression of genomic regions associated with a disease tolerant phenotype.

Alfalfa plants comprising one or more introgressed regions associated with a desired phenotype wherein at least 10%, 25%, 50%, 75%, 90%, or 99% of the remaining genomic sequences carry markers characteristic of the germplasm are also provided. Alfalfa plants comprising an introgressed region comprising regions closely linked to or adjacent to the genomic regions and markers provided herein and associated with an anthracnose disease resistance phenotype are also provided.

As an alternative to standard breeding methods of introducing traits of interest (e.g., introgression), biotechnological approaches can also be used. In one embodiment, marker-assisted technologies may be implemented to identify plants having a desired anthracnose disease resistance phenotype. Certain aspects of the invention also provide transgenic plant cells having stably integrated recombinant DNA constructs, transgenic plants and seeds comprising a plurality of such transgenic plant cells and transgenic pollen of such plants. In specific embodiments, recombinant DNA constructs integrated into an alfalfa plant according to the invention may possess enhanced resistance to anthracnose or other diseases. Alternatively, such plants may possess recombinant DNA providing other traits "stacked" with an anthracnose disease resistance trait of the invention. These stacked combinations can be created by any method, including but not limited to, cross breeding of transgenic plants or multiple genetic transformations.

An anthracnose resistant locus or allele at that locus may therefore be introduced into any plant that contains any number or combination of non-transgenic or transgenic traits. Non-limiting examples of transgenic traits comprise herbicide tolerance, increased yield, insect control, fungal disease tolerance, virus tolerance, nematode tolerance, bacterial disease tolerance, altered lignin composition or content, enhanced animal and human nutrition, environmental stress resistance, increased digestibility, altered nitrogen utilization and improved seed production, among others. In one aspect, the herbicide tolerance is selected from the group consisting of glyphosate, dicamba, glufosinate, sulfonylurea, bromoxynil and norflurazon herbicides.

In particular further embodiments of the invention, methods are provided for manufacturing seed that can be used to produce a crop of transgenic or non-transgenic plants with an enhanced trait, including resistance for all of Race 1, Race 2, and Race 5 anthracnose as well as other traits. In various methods of the invention, producing such plants may comprise one or more of the following steps: (a) screening a population of plants for an enhanced trait, where individual plants in the population can exhibit the trait at a level less than, essentially the same as, or greater than the level that the trait is exhibited in control plants, (b) selecting from the population one or more plants that exhibit the trait at a level greater than the level that said trait is exhibited in control plants, (c) collecting seed from a selected plant. In particular embodiments, the method may comprise verifying that one or more polymorphisms associated with the trait are present. In one embodiment, identifying the presence of a trait may involve detecting the presence of a marker polynucleotide molecule.

Other aspects of the various embodiments of the invention include plants, seeds, and plant parts of a plant of the invention that comprises the anthracnose disease resistance trait described herein. Plant products and byproducts derived therefrom are also provided. In specific embodiments, such plant parts and derivatives may be defined as comprising at least one marker polynucleotide molecule.

III. Development of Disease Resistant Alfalfa Varieties

For most breeding objectives, commercial breeders work within germplasm that is "cultivated type" or "elite." This germplasm is easier to breed because it generally performs well when evaluated for horticultural performance. Numerous elite alfalfa crop cultivated varieties (cultivars) have been developed. However, the performance advantage a cultivated or elite germplasm provides can be offset by a lack of allelic diversity. Breeders generally accept this tradeoff because progress is faster when working with cultivated material than when breeding with genetically diverse sources.

The process of introgressing desirable resistance genes from non-cultivated lines into elite cultivated lines while avoiding problems with linkage drag or low heritability is a long and often arduous process. Success in deploying alleles derived from wide sources therefore strongly depends on minimal or truncated introgressions that lack detrimental effects and reliable assays that preferably replace phenotypic screens. Success is further defined by simplifying genetics for key attributes to allow focus on genetic gain for quantitative traits such as disease resistance. Moreover, the process of introgressing genomic regions from non-cultivated lines can be greatly facilitated by the availability of informative markers.

One of skill in the art would therefore understand that the alleles, polymorphisms, and markers provided by the invention allow the tracking and introduction of any of the genomic regions identified herein into any genetic background to which an alfalfa species can be crossed. In addition, the genomic regions associated with disease resistance disclosed herein can be introgressed from one genotype to another and tracked phenotypically or genetically. Thus, Applicants' development of markers for the selection of the disease resistance facilitates the development of alfalfa plants having beneficial phenotypes. For example, plants and seeds can be genotyped using the markers of the present invention in order to develop varieties comprising desired disease resistance. Moreover, marker-assisted selection (MAS) allows identification of plants which are homozygous or heterozygous the desired introgression.

Meiotic recombination is essential for plant breeding because it enables the transfer of favorable alleles across genetic backgrounds, the removal of deleterious genomic fragments, and pyramiding traits that are genetically tightly linked. In the absence of accurate markers, limited recombination forces breeders to enlarge segregating populations for progeny screens. Moreover, phenotypic evaluation is time-consuming, resource-intensive and not reproducible in every environment, particularly for traits like disease resistance. The markers provided by the invention offer an effective alternative and therefore represent a significant advance in the art.

IV. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Vegetable breeders use molecular markers to interrogate a crop's genome and classify material based on genetic, rather than phenotypic, differences. Advanced marker technologies are based on genome sequences, the nucleotide order of distinct, polymorphic genotypes within a species. Such platforms enable selection for horticultural traits with markers linked to favorable alleles, in addition to the organization of germplasm using markers randomly distributed throughout the genome. In the past, a priori knowledge of the genome lacked for major vegetable crops that now have been sequenced. Scientists exploited sequence homology, rather than known polymorphisms, to develop marker platforms. Man-made DNA molecules are used to prime replication of genome fragments when hybridized pair-wise in the presence of a DNA polymerase enzyme. This synthesis, regulated by thermal cycling conditions that control hybridization and replication of DNA strands in the polymerase chain reaction (PCR) to amplify DNA fragments of a length dependent on the distance between each primer pair. These fragments are then detected as markers and commonly known examples include AFLP and RAPD. A third technique, RFLP does not include a DNA amplification step. Amplified fragment length polymorphism (AFLP) technology reduces the complexity of the genome. First, through digestive enzymes cleaving DNA strands in a sequence-specific manner. Fragments are then selected for their size and finally replicated using selective oligonucleotides, each homologous to a subset of genome fragments. As a result, AFLP technology consistently amplifies DNA fragments across genotypes, experiments and laboratories.

Polymorphisms comprising as little as a single nucleotide change can be assayed in a number of ways. For example, detection can be made by electrophoretic techniques including a single strand conformational polymorphism, denaturing gradient gel electrophoresis, or cleavage fragment length polymorphisms, but the widespread availability of DNA sequencing often makes it easier to simply sequence amplified products directly. Once the polymorphic sequence difference is known, rapid assays can be designed for progeny testing, typically involving some version of PCR amplification of specific alleles, or PCR amplification of multiple specific alleles.

Polymorphic markers serve as useful tools for assaying plants for determining the degree of identity of lines or varieties. These markers form the basis for determining associations with phenotypes and can be used to drive genetic gain. In certain embodiments of methods of the invention, polymorphic nucleic acids can be used to detect in an alfalfa plant a genotype associated with disease resistance, identify an alfalfa plant with a genotype associated with disease resistance, and to select an alfalfa plant with a genotype associated with disease resistance. In certain embodiments of methods of the invention, polymorphic nucleic acids can be used to produce an alfalfa plant that comprises in its genome an introgressed locus associated with disease resistance. In certain embodiments of the invention, polymorphic nucleic acids can be used to breed progeny an alfalfa plants comprising a locus associated with disease resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e., for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with disease resistance.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) using primer pairs that are capable of hybridizing to the proximal sequences that define a polymorphism in its double-stranded form. Methods for typing DNA based on mass spectrometry can also be used.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz, et al., *Genome Res.* 13:513-523, 2003; Cui, et al., *Bioinformatics* 21:3852-3858, 2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, CT), Agencourt Bioscience (Beverly, MA), Applied Biosystems (Foster City, CA), LI-COR Biosciences (Lincoln, NE), NimbleGen Systems (Madison, WI), Illumina (San Diego, CA), and VisiGen Biotechnologies (Houston, TX). Such nucleic acid sequencing technologies comprise formats such as parallel bead arrays, sequencing by ligation, capillary electrophoresis, electronic microchips, "biochips," microarrays, parallel microchips, and single-molecule arrays.

V. Alfalfa Variety C0416C4164

The results of an objective evaluation of the C0416C4164 alfalfa variety are presented below, in Table 1. Those of skill in the art will recognize that these are typical values that may vary due to environment and that other values that are substantially equivalent are within the scope of the invention.

TABLE 1

Phenotypic Description of C0416C4164 Alfalfa

1. FALL DORMANCY
NAAIC Protocol - Regrowth Score

| Testing Institution and Location | Date of Last Cut | Date Regrowth Scored | Application Variety C0416C4164 | Moderately Dormant ('Excalibur', 'Du Puits', '555', 'Archer') | Moderately Dormant ('Saranac', 'WL 316', 'Legend', 'G2852') | Dormant ('Ranger', 'Arrow', 'WL 317', 'WL325HQ') | LSD .05 | CV | x̄ |
|---|---|---|---|---|---|---|---|---|---|
| Forage Genetics International - West Salem, WI | Sep. 14, 2016 | Oct. 4, 2016 | 5.6 | 5.0 | 6.0 | 6.8 | 0.48 | 7.4 | 6.0 |
| Forage Genetics International - Boone, WI | Sep. 14, 2016 | Oct. 5, 2016 | 5.4 | 5.0 | 6.0 | 7.0 | 0.49 | 7.5 | 5.9 |

2. DISEASE RESISTANCE - Anthracnose (Race 1) (*Colletotrichum trifolii*)
NAAIC Protocol
Forage Genetics International - Nampa, ID - Greenhouse - 2016

| Variety | Resistance/Class Expected Value | Syn. Gen. Tested | Unadjusted % Resistance | Number of Plants Tested | LSD .05 | CV | x̄ |
|---|---|---|---|---|---|---|---|
| C0416C4164 | HR 59% | Syn 1 | 48% | 200 | 9.0% | 17.1% | 37% |
| 'Arc' | HR 65% | | 54% | | | | |
| 'Sarnac' | S 2% | | 2% | | | | |

3. DISEASE RESISTANCE - Aphanomyces Root Rot (Race 1) (*Aphanomyces euteiches*)
NAAIC Protocol
Forage Genetics International - West Salem, WI - Greenhouse - 2016

| Variety | Resistance/Class Expected Value | Syn. Gen. Tested | Unadjusted % Resistance | Number of Plants Tested |
|---|---|---|---|---|
| C0416C4164 | HR 61% | Syn 1 | 57% | 200 |
| 'WAPH-1' | R 50% | | 47% | |
| 'Saranac' | S 1% | | 0% | |

TABLE 1-continued

Phenotypic Description of C0416C4164 Alfalfa

4. DISEASE RESISTANCE - Aphanomyces Root Rot (Race 2) (*Aphanomyces euteiches*)
NAAIC Protocol
Forage Genetics International - West Salem, WI - Greenhouse - 2017

| Variety | Resistance/Class Expected Value | Syn. Gen. Tested | Unadjusted % Resistance | Number of Plants Tested | LSD .05 | CV | $\bar{x}$ |
|---|---|---|---|---|---|---|---|
| C0416C4164 | HR 56% | Syn 1 | 56% | 200 | 9.6% | 11.1% | 53% |
| 'WAPH-5' | R 50% | | 50% | | | | |
| 'Saranac' | S 1% | | 0% | | | | |
| 'WAPH-1' | S 1% | | 0% | | | | |

5. DISEASE RESISTANCE - Phytophthora Root Rot (*Phytophthora megasperma* f. *medicaginis*)
NAAIC Protocol
Forage Genetics International - West Salem, WI - Greenhouse - 2016

| Variety | Resistance/Class Expected Value | Syn. Gen. Tested | Unadjusted % Resistance | Number of Plants Tested | LSD .05 | CV | $\bar{x}$ |
|---|---|---|---|---|---|---|---|
| C0416C4164 | HR 57% | Syn 1 | 53% | 150 | 11.2% | 13.3% | 51% |
| 'WAPH-1' | R 55% | | 51% | | | | |
| 'Saranac' | S 3% | | 4% | | | | |

6. DISEASE RESISTANCE - Anthracnose (Race 5)
NAAIC Protocol
Greenhouse - 2016

| Variety | Syn. Gen. Tested | Unadjusted % Resistance | Number of Plants Tested | LSD .05 | CV | $\bar{x}$ |
|---|---|---|---|---|---|---|
| C0416C4164 | Syn 1 | 71% | 200 | 8.1% | 20.4% | 25.9% |
| 'Arc' | | 7% | | | | |
| 'Saranac AR' | | 12% | | | | |
| 'Saranac' | | 2% | | | | |

VI. Alfalfa Variety H0415C4114

The results of an objective evaluation of the H0415C4114 alfalfa variety are presented below, in Table 2. Those of skill in the art will recognize that these are typical values that may vary due to environment and that other values that are substantially equivalent are within the scope of the invention.

TABLE 2

Phenotypic Description of H0415C4114 Alfalfa

1. FALL DORMANCY
NAAIC Protocol - Regrowth Score

| Testing Institution and Location | Date of Last Cut | Date Regrowth Scored | Regrowth Score | | | | | | |
|---|---|---|---|---|---|---|---|---|---|
| | | | Application Variety H0415C4114 | Check Varieties | | | LSD .05 | CV | $\bar{x}$ |
| | | | | Moderately Dormant ('Archer') | Moderately Dormant ('G2852') | Dormant ('WL325HQ') | | | |
| Forage Genetics International - West Salem, WI | Sep. 8, 2015 | Oct. 6, 2015 | 5.5 | 5.3 | 6.0 | 6.9 | 0.49 | 7.0 | 4.4 |
| Forage Genetics International - Boone, IA | Sep. 11, 2015 | Oct. 2, 2015 | 5.8 | 4.9 | 6.0 | 6.9 | 0.32 | 4.6 | 4.3 |

2. DISEASE RESISTANCE - Anthracnose (Race 1) (*Colletotrichum trifolii*)
NAAIC Protocol
Forage Genetics International - Nampa, ID - Greenhouse - 2015

| Variety | Resistance/Class Expected Value | Syn. Gen. Tested | Unadjusted % Resistance | Number of Plants Tested | LSD .05 | CV | $\bar{x}$ |
|---|---|---|---|---|---|---|---|
| H0415C4114 | HR 71% | Syn1 | 78% | 200 | 9% | 9% | 76% |
| 'Arc' | HR 65% | | 71% | | | | |
| 'Sarnac' | S 4% | | 4% | | | | |

TABLE 2-continued

Phenotypic Description of H0415C4114 Alfalfa

3. DISEASE RESISTANCE - Aphanomyces Root Rot (Race 1) (*Aphanomyces euteiches*)
NAAIC Protocol
Forage Genetics International - West Salem, WI - Greenhouse - 2015

| Variety | Resistance/Class Expected Value | Syn. Gen. Tested | Unadjusted % Resistance | Number of Plants Tested | LSD .05 | CV | $\bar{x}$ |
|---|---|---|---|---|---|---|---|
| H0415C4114 | HR 66% | Syn1 | 58% | 200 | 5% | 6% | 62% |
| 'WAPH-1' | R 50% | | 44% | | | | |
| 'Saranac' | S 1% | | 5% | | | | |

4. DISEASE RESISTANCE - Aphanomyces Root Rot (Race 2) (*Aphanomyces euteiches*)
NAAIC Protocol
Forage Genetics International - West Salem, WI - Greenhouse - 2015

| Variety | Resistance/Class Expected Value | Syn. Gen. Tested | Unadjusted % Resistance | Number of Plants Tested | LSD .05 | CV | $\bar{x}$ |
|---|---|---|---|---|---|---|---|
| H0415C4114 | HR 58% | Syn1 | 42% | 200 | 2% | 5% | 41% |
| 'WAPH-5' | R 50% | | 36% | | | | |
| 'Saranac' | S 1% | | 3% | | | | |
| 'WAPH-1' | S 0% | | 0% | | | | |

5. DISEASE RESISTANCE - Bacterial Wilt (*Clavibacter michiganese*)
NAAIC Protocol
Forage Genetics International - West Salem, WI - Field - 2016

| Variety | Resistance/Class Expected Value | Syn. Gen. Tested | Unadjusted % Resistance | Number of Plants Tested | LSD .05 | CV | $\bar{x}$ |
|---|---|---|---|---|---|---|---|
| H0415C4114 | HR 77% | Syn1 | 67% | 200 | 13% | 20% | 48% |
| 'Vernal' | R 42% | | 37% | | | | |
| 'Sonora' | S 1% | | 0% | | | | |

6. DISEASE RESISTANCE - Phytophthora Root Rot (*Phytophthora megasperma* f. *medicaginis*)
NAAIC Protocol
Forage Genetics International - West Salem, WI - Greenhouse - 2015

| Variety | Resistance/Class Expected Value | Syn. Gen. Tested | Unadjusted % Resistance | Number of Plants Tested | LSD .05 | CV | $\bar{x}$ |
|---|---|---|---|---|---|---|---|
| H0415C4114 | HR 64% | Syn1 | 59% | 200 | 4% | 6% | 48% |
| 'WAPH-1' | R 55% | | 50% | | | | |
| 'Saranac' | S 3% | | 3% | | | | |

7. DISEASE RESISTANCE - Anthracnose (Race 5) (*Colletotrichum trifolii*)
NAAIC Protocol
Forage Genetics International - West Salem, WI - Greenhouse - 2017

| Variety | Resistance/Class Expected Value | Syn. Gen. Tested | Unadjusted % Resistance | Number of Plants Tested | LSD .05 | CV | $\bar{x}$ |
|---|---|---|---|---|---|---|---|
| H0415C4114 | R 44% | Syn1 | 44% | 200 | 17% | 36% | 30% |
| 'Saranac AR' | S 14% | | 14% | | | | |
| 'Saranac' | S 0% | | 0% | | | | |
| 'Arc' | S 0% | | 0% | | | | |

8. PEST AND DISEASE RESISTANCE - Stem Nematode (*Ditylenchus dipsaci*)
NAAIC Protocol
Forage Genetics International - Nampa, ID - Greenhouse - 2016

| Variety | Resistance/Class Expected Value | Syn. Gen. Tested | Unadjusted % Resistance | Number of Plants Tested | LSD .05 | CV | $\bar{x}$ |
|---|---|---|---|---|---|---|---|
| H0415C4114 | R 35% | Syn1 | 29% | 400 | 8% | 13% | 40% |
| 'Vernema' | R 60% | | 49% | | | | |
| 'Ranger' | S 5% | | 7% | | | | |

TABLE 2-continued

Phenotypic Description of H0415C4114 Alfalfa

9. OTHER - RoundUp Ready Tolerance
NAAIC Protocol
Forage Genetics International - Touchet, WA - Greenhouse - 2015

| Variety | Resistance/Class Expected Value | Syn. Gen. Tested | Unadjusted % Resistance | Number of Plants Tested | LSD .05 | CV | x̄ |
|---|---|---|---|---|---|---|---|
| H0415C4114 | HT 89% | Syn1 | 87% | 800 | 4% | 3% | 85% |
| 'FGI-RR90' | HT 90% | | 89% | | | | |
| 'Saranac' | S 0% | | 0% | | | | |

VII. Additional Alfalfa Lines

In one embodiment of the invention, a plant is provided that comprises the anthracnose resistance trait found in plants of which representative seeds were deposited under American Type Culture Collection (ATCC) Accession No. PTA-124210. In another embodiment, a plant of the invention is provided which is defined as sharing an ancestral genetic source for the anthracnose resistance trait found in plants for which such representative seed were deposited. In still yet another embodiment of the invention, a plant comprising the anthracnose resistance trait is the alfalfa line C0416C4164 or a progeny thereof that inherited the anthracnose resistance trait therefrom.

Another aspect of the invention provides methods for crossing the alfalfa line C0416C4164 with itself or a second plant and the seeds and plants produced by such methods. These methods can be used for propagation of line C0416C4164, or can be used to produce hybrid alfalfa seeds and the plants grown therefrom. Hybrid seeds are produced by crossing line C0416C4164 with second alfalfa parent line.

In another embodiment of the invention, a plant is provided that comprises the anthracnose resistance trait found in plants of which representative seeds were deposited under American Type Culture Collection (ATCC) Accession No. PTA-125043. In another embodiment, a plant of the invention is provided which is defined as sharing an ancestral genetic source for the anthracnose resistance trait found in plants for which such representative seed were deposited. In still yet another embodiment of the invention, a plant comprising the anthracnose resistance trait is the alfalfa line H0415C4114 or a progeny thereof that inherited the anthracnose resistance trait therefrom.

Another aspect of the invention provides methods for crossing the alfalfa line H0415C4114 with itself or a second plant and the seeds and plants produced by such methods. These methods can be used for propagation of line H0415C4114, or can be used to produce hybrid alfalfa seeds and the plants grown therefrom. Hybrid seeds are produced by crossing line H0415C4114 with second alfalfa parent line.

In another aspect, the present invention provides a method of introgressing an anthracnose resistance trait into an alfalfa plant comprising: (a) crossing at least a first alfalfa line having increased anthracnose resistance with a second alfalfa line to form a segregating population; (b) screening the population for anthracnose resistance; and (c) selecting at least one member of the population having an increased or altered anthracnose resistance.

VIII. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which alfalfa plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, the term "transgenic plant" means a plant that comprises within its cells a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette.

As used herein, the term "transgenic" means any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extrachromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

As used herein, the term "plant part" includes a cell, a seed, a root, a stem, a leaf, a head, a flower, or pollen, as well as any other part or portion of a plant.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite line" or "cultivated line" means any line that has resulted from breeding and selection for superior agronomic performance. An "elite plant" refers to a plant belonging to an elite line. Numerous elite lines are available and known to those of skill in the art of alfalfa breeding. An "elite population" is an assortment of elite individuals or lines that can be used to represent the state of the art in terms of agronomically superior genotypes of a given crop species, such as an alfalfa line. Similarly, an "elite germplasm" or elite strain of germplasm is an agronomically superior germplasm.

As used herein, the term "introgressed," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the terms "recombinant" or "recombined" in the context of a chromosomal segment refer to recombinant DNA sequences comprising one or more genetic loci in a configuration in which they are not found in nature, for example as a result of a recombination event between homologous chromosomes during meiosis.

As used herein, the term "linked," when used in the context of nucleic acid markers and/or genomic regions, means that the markers and/or genomic regions are located on the same linkage group or chromosome such that they tend to segregate together at meiosis.

As used herein, "resistance locus" means a locus associated with resistance or tolerance to disease. For instance, a resistance locus according to the present invention may, in one embodiment, control resistance or susceptibility to black rot.

As used herein, "resistance allele" means the nucleic acid sequence associated with resistance or tolerance to disease.

As used herein "resistance" or "improved resistance" in a plant to disease conditions is an indication that the plant is less affected by disease conditions with respect to yield, survivability and/or other relevant agronomic measures, compared to a less resistant, more "susceptible" plant. Resistance is a relative term, indicating that a "resistant" plant survives and/or produces better yields in disease conditions compared to a different (less resistant) plant grown in similar disease conditions. As used in the art, disease "tolerance" is sometimes used interchangeably with disease "resistance." One of skill will appreciate that plant resistance to disease conditions varies widely, and can represent a spectrum of more-resistant or less-resistant phenotypes. However, by simple observation, one of skill can generally determine the relative resistance or susceptibility of different plants, plant lines or plant families under disease conditions, and furthermore, will also recognize the phenotypic gradations of "resistant."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

IX. Deposit Information

A deposit was made of at least 2500 seeds of C0416C4164 Alfalfa, as described herein. The deposit was made with the American Type Culture Collection (ATCC), 10801 University Boulevard, Manassas, Va. 20110-2209 USA. The deposit is assigned ATCC Accession No. PTA-124210, and the date of deposit was May 23, 2017. Access to the deposit will be available during the pendency of the application to persons entitled thereto upon request. The deposit will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

A deposit was made of at least 2500 seeds of H0415C4114 Alfalfa, as described herein. The deposit was made with the American Type Culture Collection (ATCC), 10801 University Boulevard, Manassas, Va. 20110-2209 USA. The deposit is assigned ATCC Accession No. PTA-125043, and the date of deposit was Apr. 3, 2018. Access to the deposit will be available during the pendency of the application to persons entitled thereto upon request. The deposit will be maintained in the ATCC Depository, which is a public depository, for a period of 30 years, or 5 years after the most recent request, or for the enforceable life of the patent, whichever is longer, and will be replaced if nonviable during that period. Applicant does not waive any infringement of their rights granted under this patent or any other form of variety protection, including the Plant Variety Protection Act (7 U.S.C. 2321 et seq.).

X. Examples

Example 1

Identification of Emerging Anthracnose Race

Low levels of anthracnose symptoms were observed in field trials of alfalfa varieties resistant to Race 1 and Race 2 anthracnose. The pathogen was cultured and used to inoculate Saranac AR seedlings (Saranac AR is an approved resistant line for both Race 1 and Race 2 anthracnose). In this initial test, no resistant Saranac AR plants were observed, suggesting the development of a new race of the pathogen.

A screening of proprietary breeding populations for resistance to the new pathogen was thus initiated. Although low levels of resistance were found in a few breeding populations, almost all of these "resistant" plants succumbed to the disease 1-2 months later. This latent infection and late symptom development on seedlings is very uncharacteristic for Race 1 and Race 2 anthracnose. These results indicated that previously known resistance to anthracnose was not effective against the new race, identified as Race 5.

Example 2

Anthracnose Screening Assay

A systematic study was developed to assess the effect of several variables in the standard anthracnose screening process. Variables evaluated included the use of inoculum from the new race of the pathogen, inoculum concentration, length of incubation time, and timing of selection of resistant plants. This led to the development of an assay that accurately identified anthracnose resistance, allowing for the identification of plants comprising resistance to the newly identified anthracnose race.

To develop the assay, a needle inoculation procedure was performed. In the needle inoculation procedure, plants having stems of approximately 10 inches or longer were selected. The stems were taped at least 8 inches above the soil to prevent the disease from spreading into the roots. Inoculum was prepared by swirling 1 drop of tween with 100 mL of distilled water in a beaker. The swirled solution was then poured into dishes of anthracnose spores. A rubber scarper was used to incorporate the spores into the solution. The spore containing solution was then poured back into the beaker through a filter. A concentration of conidia of between $1 \times 10^6$ and $2 \times 10^6$ was confirmed. A full needle of solution was then inserted above the tape on the plants. A small amount of solution was injected into the stem. The plants were housed in a greenhouse and watered on a routine watering schedule. Seven days after inoculation, the stems of the plants were assessed. A % susceptibility and resistance was determined by examining and counting individual plants. Susceptible plants demonstrated diamond lesion, shepherds, or spreading disease upon visual inspection of a stem. Resistant plants demonstrated no spreading disease; in some instance they exhibited a scar from the site of needle puncture.

An anthracnose race inoculation was also performed for anthracnose. Flats of approximately 14 day old seedlings (or seedlings of approximately 3 inches in height) were water and allowed today for approximately 2 hours. A 1 L spray bottle containing an anthracnose solution of 50,000 spores/L of distilled water was applied to the flats of alfalfa until run-off, which was approximately 5-10 mL per flat. The flats were covered with a 1020 no hole flat and the flats were taped together, and the tape was crimped for secure the edges of the flats. The flats were stored in a dark, room temperature area for 48 hours. After 48 hours, the flat covers were removed, and the plants were scored according to CPR0057AZM Devitalization and Final Disposition. Plants that were free of disease were transferred to individual peat cups for breeding purposes.

Example 3

Identification of Race 5 Anthracnose-Resistant Lines

In Year 1, phenotypic screen of fall dormancy 4-5 germplasm was conducted, and a very low frequency (<1%) of plants resistant to Race 5 anthracnose was observed in five breeding lines. Lines exhibiting low levels of resistance to Race 5 were advanced to the next cycle of evaluation. Resistance to Race 5 anthracnose was confirmed, and escapes eliminated, with stem inoculations of these lines using Race 5 anthracnose. A single cycle of phenotypic selection led to the development of novel breeding populations with >31% resistant plants. Segregation ratios during this breeding process suggest a single gene, with partial dominance that provides resistance to Race 1, Race 2 and the new Race 5.

Example 4

Evaluation of Race 5 Anthracnose Resistance in Identified Lines

Seed was produced from several of the new Race 5-resistant breeding populations. Seed was harvested in late July which allowed planting in multiple location forage yield trials in mid-August of Year 2. The Year 3 growing season exhibited significant rainfall at the trial locations and Race 5 anthracnose symptoms were very severe.

At one trial location, a fungicide study using broad spectrum fungicide Headline™ (BASF, Research Triangle Park, North Carolina) was conducted wherein the fungicide was applied to Race 5-susceptible varieties after each harvest during the season, and compared to a non-sprayed control. In Year 3, a 20-25% increase in forage yield with fungicide treatment was demonstrated in the third and fourth harvest, when anthracnose symptoms are typically most severe. In the fall of Year 2, established trials at multiple locations demonstrated significant anthracnose symptoms early July to mid-October on all entries, except for the new Race 5-resistant experimental varieties, which were disease free. At all three locations the new Race 5-resistant experimental varieties, conventional, Roundup Ready, and HarvXtra exhibited significantly higher yield in the last two harvests than their susceptible counterparts and all commercial control varieties.

The average yield advantage for Race 5-resistant varieties in these Year 2 harvests was 15-20%. The disease resistance evaluations are summarized in FIG. 1. In FIG. 1, 412M107 is a control variety with anthracnose resistance typical of modern commercial cultivars.

Table 3 shows results from a Year 2 forage yield trial conducted at Location 1. Check 1 is the average yield of 3 check varieties (Attention II, Hi-gest360, and HyburFOrce 3400). Check 2 is the average yield of 2 check vanities (54R02) and WL372HQ. In both Tables 3 and 4, "Cony" indicates experimental varieties without genetically engineered traits and "RRA+H" indicates experimental varieties with either the HarvXtra and/or Roundup Ready traits.

TABLE 3

Anthracnose Screen of Experimental Plants for Year 1 Forage Yield Trials at Location 1.
Anthracnose Screened Experimentals Compared to GE Check Classes

| Checks | AnExps | #Experimentals | Avg Yld Dis Scm T/A | | | | % Check | | | |
|---|---|---|---|---|---|---|---|---|---|---|
| | | | Cut 1 | Cut 2 | Cut 3 | Cut 4 | Cut 1 | Cut 2 | Cut 3 | Cut 4 |
| Check 1 | Conv | 12 | 2.63 | 2.41 | 2.32 | 1.78 | 0.91 | 1.01 | 1.15 | 1.46 |
| Check 2 | RRA + H | 8 | 2.56 | 2.29 | 2.15 | 1.63 | 0.94 | 0.95 | 1.00 | 1.28 |

Table 4 shows results from the Year 2 forage yield trial conducted at Location 2.

TABLE 4

Anthracnose Screen of Experimental Plants for Year 2 Forage Yield Trials at Location 2.
Anthracnose Screened Experimentals Compared to GE Check Gasses

| Checks | AnExps | # Experimentals | Avg Yld Dis Scm T/A | | | | | % Check | | | | |
|---|---|---|---|---|---|---|---|---|---|---|---|---|
| | | | Cut 1 | Cut 2 | Cut 3 | Cut 4 | Cut 5 | Cut 1 | Cut 2 | Cut 3 | Cut 4 | Cut 5 |
| Check 1 | Conv | 12 | 2.10 | 2.04 | 1.48 | 1.37 | 0.77 | 0.89 | 1.03 | 1.26 | 1.26 | 1 24 |
| Check 2 | RRA + H | 8 | 1.87 | 1.90 | 1 36 | 1.27 | 0.72 | 0.83 | 0.94 | 1.04 | 1.15 | 0.99 |

Example 5

Development of Race 5 Anthracnose-Resistant Lines

Figure 2:
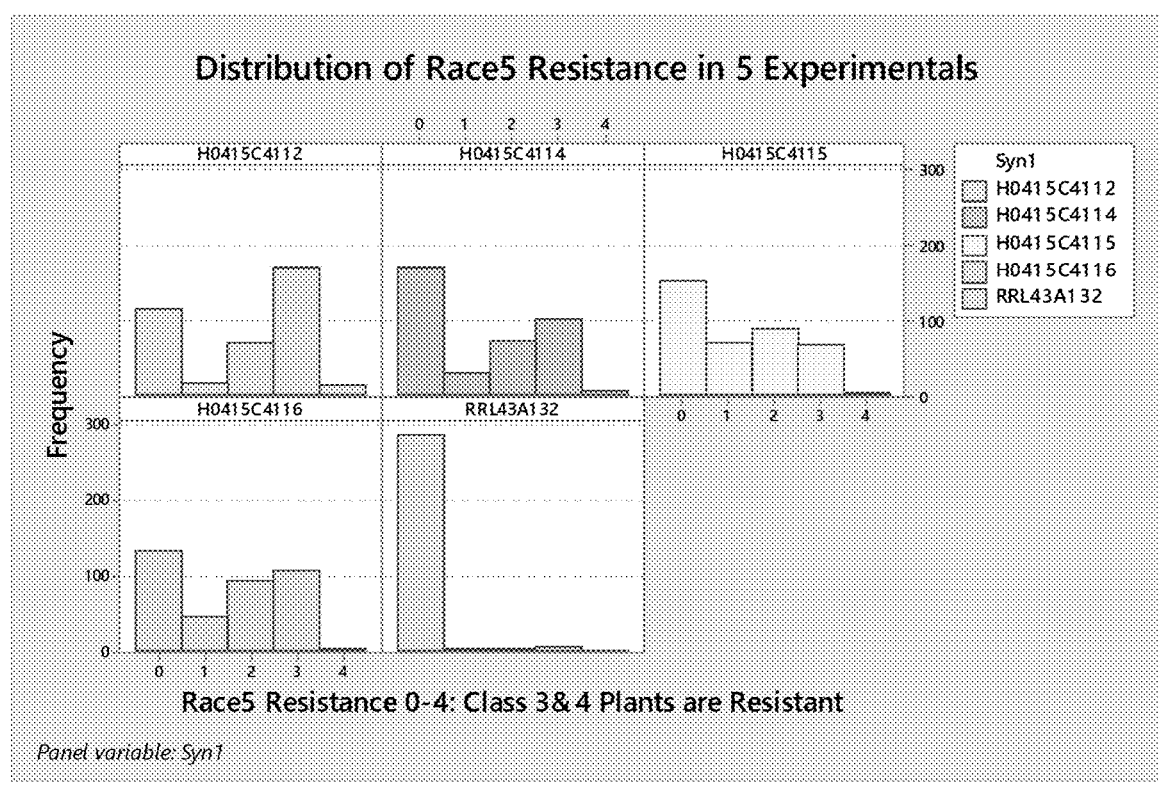
FIG. 2: Illustrates an experiment comparing source founder population for race 5 anthracnose (RRL43A132) to derived populations (Synthetics) which are a subset of the experimental varieties that were developed for race 5 anthracnose resistance. A rating of 0 indicates plant dead and a rating of 4 indicates significant resistant. The graph shows the distribution of individual plants within the population. These populations were subject to 1 cycle of recurrent selection for race 5 anthracnose resistance. Plants scored as a 3 or 4 are considered resistant.

FIG. 2 shows a comparison of a founder population for race 5 anthracnose (RRL43A132, a susceptible plant) to derived populations having race 5 anthracnose resistance introgressed in HarvXtra (H0415C4112, H0415C4114, H0415C4115, and H0415C4116).

Race 5 resistance is score from 0 to 4, wherein 0 indicated dead plants, and 4 indicates highly resistant plants. FIG. 2 shows the distribution of individual plants within each population. These populations have had 1 cycle of recurrent selection for Race 5 anthracnose resistance. Plants scored as a 3 or 4 were considered resistant.

Figure 3A:
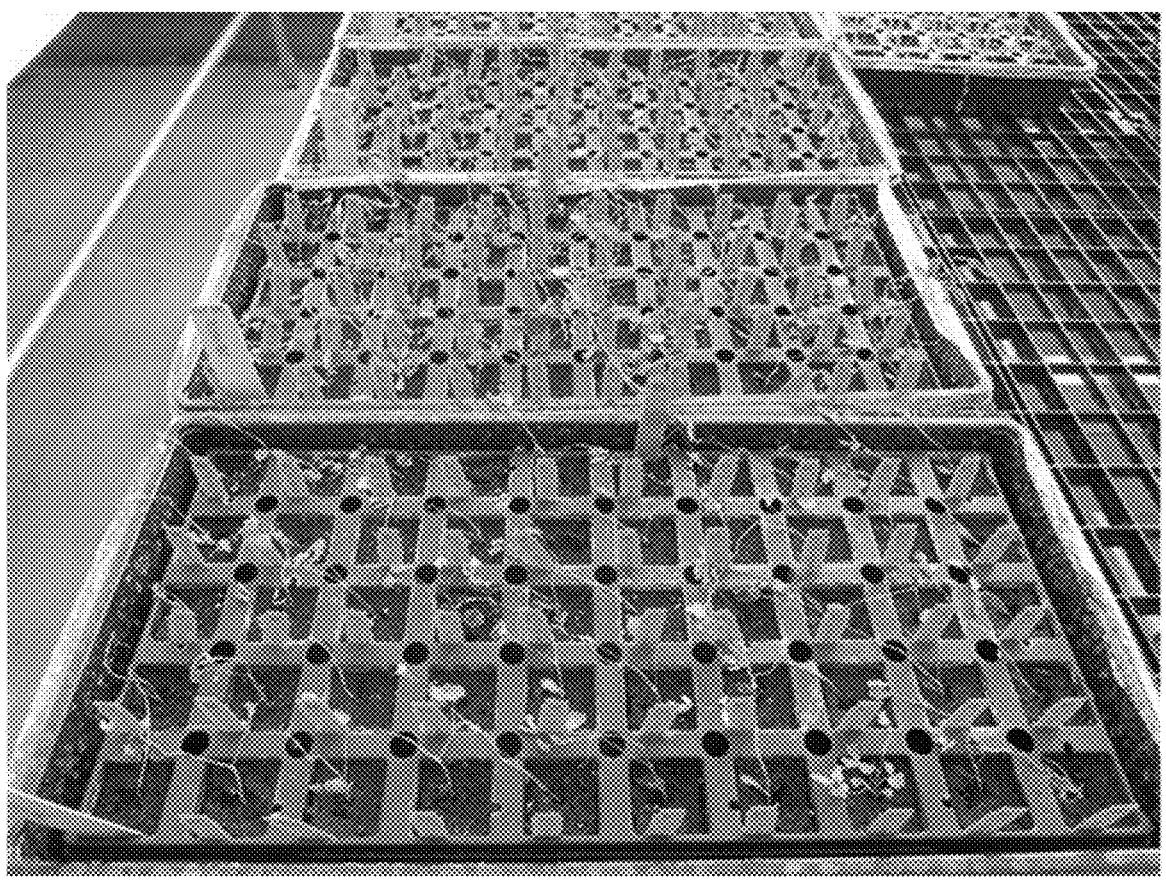
FIG. 3A: Illustrates that all RRL43A132 alfalfa 13 days after inoculation with Race 5 anthracnose, are dead. RRL43A132 is the source population that led to many of the derived anthracnose Race 5 resistant experimental plants.

FIG. 3A illustrates that all RRL43A132 plants were dead 13 days after inoculation with Race 5 anthracnose. RRL43A132 is the source population that led to many of the derived anthracnose Race 5 HarvXtra resistant experimentals.

Figure 3B:
FIG. 3B: Illustrates that H0416C4116 alfalfa 13 days after inoculation with Race 5 anthracnose yielded a large percentage of survivors compared to the founder population (this population has had 1 cycle of phenotypic selection for Race 5 anthracnose resistance).

FIG. 3B illustrates that H0416C4116 alfalfa 13 days after inoculation with Race 5 anthracnose yielded a large percentage of survivors compared to the founder population (this population has had 1 cycle of phenotypic selection for Race 5 anthracnose resistance).

Example 6

Anthracnose Race 5 Resistance Locus Identification

Molecular markers associated with a QTL conferring resistance to anthracnose race 5 were identified by associating genetic variations observed to resistant and susceptible individuals. Nine synthetic (Syn1) alfalfa populations were studied: three conventional populations (C0415C4152, C0415C4159, C0415C4360), three Roundup Ready populations (R0415C3354, R0415C4156, R0415C4355) and three HarvXtra populations (H0415C4112, H0415C4114, H0415C4115). Seeds were planted in a greenhouse and seedlings were evaluated for Anthracnose Race 5 resistance by the method of Nichole O'Neill (NAAIC Standard Test, 1991). Each plant was scored as phenotypically as 'resistant' or 'susceptible'.

Genotyping-by-Sequencing (GBS) methods were used to generate SNP markers associated with the anthracnose race 5 resistance QTL, based on the phenotypic evaluation performed above. DNA was extracted from lyophilized leaf tissue using the DNeasy 96 Plant Kit (Qiagen, 69181) per manufacturer's instructions. Extracted DNA samples were quantified using the Quant-iT PicoGreen dsDNA Assay Kit (Invitrogen, P7589) prior to normalization. GBS libraries were constructed by the Elshire et al. (2011) method with minor modification. 100 ng of DNA from each sample was digested with ApeKI (New England Biolabs, R0643L) and ligated with T4 DNA ligase (NEB, M0202L) to a common adaptor and a unique barcoded adapter. Pooled samples were purified using the QIAquick PCR Purification Kit (QIAGEN, 28104) and quantified again with the Quant-iT PicoGreen dsDNA Assay Kit. Each pool was amplified with Library Amplification Readymix (KAPA Biosystems, KK2611) and two 5 uM primers using the following PCR program: 5 min at 72° C., 30 s at 98° C., 10 cycles (10 s at 98° C., 30 s at 65° C., 30 s at 72° C.), 5 min at 72° C. PCR products were purified using the QIAquick PCR Purification Kit. Each library was sequenced on the Illumina HiSeq4000.

Raw GBS data were processed using the SNP CROP pipeline v.3.0 (Melo et al., 2016). Alignment and localization of the anthracnose race 5 resistance QTL was carried out using the publicly available *Medicago truncatula* reference genome JCVI.Medtr.v4.20130313. Only bi-allelic SNPs present in at least 50% of individuals in the mapping population were considered in the mapping marker set, resulting in a total of 5065 SNPs. The statistical association analysis was carried out using a mixed model framework (i.e. Q+K GWA mixed model) via the GWASpoly R package (Rosyara et al., 2016). The results indicated the presence of a significant anthracnose race 5 resistance QTL located on chromosome 4. Table 5 shows SNP markers identified as being associated with anthracnose race 5 resistance from a joint analysis of the HarvXtra populations.

TABLE 5

HarvXtra Joint Analysis Marker Results

| Marker | Chromosome | Position (bp) | −log(p-value) |
|---|---|---|---|
| FG2196 | 4 | 14,130,374 | 5.55 |
| FG2197 | 4 | 14,130,386 | 5.55 |
| FG2201 | 4 | 15,513,183 | 8.27 |
| FG2208 | 4 | 16,945,124 | 6.37 |
| FG2218 | 4 | 16,968,138 | 19.23 |
| FG2226 | 4 | 17,411,203 | 42.00 |
| FG2274 | 4 | 23,797,145 | 5.80 |
| FG2337 | 4 | 27,310,905 | 4.36 |

Table 6 shows SNP markers identified as being associated with anthracnose race 5 resistance from a joint analysis of the Roundup Ready populations.

TABLE 6

Roundup Ready Joint Analysis Marker Results

| Marker | Chromosome | Position (bp) | −log(p-value) |
|---|---|---|---|
| FG27232 | 4 | 19,197,732 | 13.13 |
| FG2724 | 4 | 19,197,756 | 5.29 |
| FG27251 | 4 | 19,197,832 | 6.57 |
| FG27271 | 4 | 19,292,176 | 6.96 |

Table 7 shows SNP markers identified as being associated with anthracnose race 5 resistance from a joint analysis of the Conventional populations.

TABLE 7

Conventional Joint Analysis Marker Results

| Marker | Chromosome | Position (bp) | −log(p-value) |
|---|---|---|---|
| FG2218 | 4 | 16,968,138 | 5.98 |
| FG27062 | 4 | 17,408,441 | 6.19 |
| FG27232 | 4 | 19,197,732 | 9.98 |

Odds ratio (OR) is among the most commonly used statistical measures of association or effect, particularly, when dependent variables are binary, such as studies of association between risk factors and disease outcomes. In this case, the OR is the odds of resistance in plants comprising the SNP divided by the odds of resistance in plants not comprising the SNP. The ORs were calculated for the SNP showing the highest significance within each of the three sets of populations.

For the HarvXtra populations, FG2226 was observed to be the SNP with the highest significance. The OR was calculated to be 102.5 ((122×126)/(10×15)), based on the data obtained in Table 8. Thus, the odds of resistance to anthracnose race 5 in plants with the allele at FG2226 is ≈102 times higher than the odds of resistance to anthracnose race 5 in plants without the allele at FG2226.

TABLE 8

Confusion Matrix for HarvXtra Joint Analysis Based on FG2226

|  | Observed = Susceptible | Observed = Resistant |
|---|---|---|
| Predicted = Susceptible | 122 | 10 |
| Predicted = Resistant | 15 | 126 |

For the Roundup Ready populations, FG27251 was observed to be the SNP with the highest significance. The OR was calculated to be 87.59 ((74×116)/(49×2)), based on the data obtained in Table 9. Thus, the odds of resistance to anthracnose race 5 in plants with the allele at FG27251 is ≈88 times higher than the odds of resistance to anthracnose race 5 in plants without the allele at FG27251.

TABLE 9

Confusion Matrix for Roundup Ready Joint Analysis Based on FG27251

|  | Observed = Susceptible | Observed = Resistant |
|---|---|---|
| Predicted = Susceptible | 74 | 49 |
| Predicted = Resistant | 2 | 116 |

For the conventional populations (C0415C4152, C0415C4159, C0415C4360), FG27251 was observed to be the SNP with the highest significance. The OR was calculated to be 16.17 ((153×52)/(6×82)), based on the data obtained in Table 10. Thus, the odds of resistance to anthracnose race 5 in plants with the allele at FG27251 is ≈16 times higher than the odds of resistance to anthracnose race 5 in plants without the allele at FG27251.

TABLE 10

Confusion Matrix for Conventional Joint Analysis Based on FG27251

|  | Observed = Susceptible | Observed = Resistant |
|---|---|---|
| Predicted = Susceptible | 153 | 82 |
| Predicted = Resistant | 6 | 52 |

The locus identified encompasses 7.9 cM on chromosome 4 and corresponds to the interval 16,945,124 bp to 19,292,176 bp of the public physical map. Table 11 lists the significant markers found to be associated with resistance to anthracnose race 5.

TABLE 11

Highly Significant SNP Markers Associated with Anthracnose Race 5 Resistance

| Marker | Marker Sequence (SEQ ID NO) | Chr. | Favorable Allele | SNP Public Position JCVI.Medtr.v4. 20130313 (bp) | Genetic Map Distance (cM) (From Li et al., 2013) |
|---|---|---|---|---|---|
| FG2208 | 1 | 4 | G | 16,945,124 | ≥24.405 |
| FG2218 | 2 | 4 | A | 16,968,138 | |
| FG27062 | 3 | 4 | A | 17,408,441 | |
| FG2226 | 4 | 4 | A | 17,411,203 | |
| FG27232 | 5 | 4 | G | 19,197,732 | |
| FG27251 | 6 | 4 | T | 19,197,832 | |
| FG27271 | 7 | 4 | A | 19,292,176 | ≤32.328 |

Example 7

Methods for Producing Anthracnose Race 5 Resistant Plants

Plants comprising broad-spectrum resistance to anthracnose may be produced by crossing a plant comprising an allele conferring anthracnose race 5 resistance, representative seed comprising said allele having been deposited under ATCC Accession No. PTA-124210 or under ATCC Accession No. PTA-125043, with a second plant to produce a progeny plant comprising said allele. Progeny plants may further be selected for the presence of said allele conferring anthracnose race 5 resistance. Selecting for the presence of said allele may include detecting at least one genetic marker within or genetically linked to an identified genomic region flanked in the genome of said plant by a first identified marker locus and a second identified marker locus. In certain examples, this includes detecting at least one polymorphism at a locus selected from the group consisting of FG2208 (SEQ ID NO: 1), FG2218 (SEQ ID NO: 2), FG27062 (SEQ ID NO: 3), FG2226 (SEQ ID NO: 4), FG27232 (SEQ ID NO: 5), FG27251 (SEQ ID NO: 6), and FG27271 (SEQ ID NO: 7).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of introgressing a *Colletotrichum trifolii* race 5 resistance allele into a synthetic population of *Medicago sativa* plants comprising:

(a) crossing a *Medicago sativa* plant comprising a *Colletotrichum trifolii* race 5 resistance allele with at least one *Medicago sativa* plant of a synthetic population lacking said allele to form a segregating population, wherein said resistance allele is located within a genomic region flanked in the genome of said plant by marker locus FG2208 (SEQ ID NO: 1) and marker locus FG27271 (SEQ ID NO: 7) on chromosome 4, wherein said resistance allele confers increased resistance to *Colletotrichum trifolii* Race 5 as compared with a plant not comprising said allele, and wherein said resistance allele comprises a marker selected from the group consisting of FG2208 (SEQ ID NO: 1), FG2218 (SEQ ID NO: 2), FG27062 (SEQ ID NO: 3), FG2226 (SEQ ID NO: 4), FG27232 (SEQ ID NO: 5), FG27251 (SEQ ID NO: 6), and FG27271 (SEQ ID NO: 7);

(b) screening the segregating population for the presence of said resistance allele; and (c) selecting at least one or more *Medicago sativa* plants from the segregating population based on the presence said resistance allele.

2. The method of claim 1, wherein screening comprises detecting an allele comprising at least one genetic marker within or genetically linked to said genomic region on chromosome 4.

3. The method of claim 2, wherein screening comprises detecting an allele comprising a marker locus selected from the group consisting of FG2208 (SEQ ID NO: 1), FG2218 (SEQ ID NO: 2), FG27062 (SEQ ID NO: 3), FG2226 (SEQ ID NO: 4), FG27232 (SEQ ID NO: 5), FG27251 (SEQ ID NO: 6), and FG27271 (SEQ ID NO: 7).

4. The method of claim 1, wherein screening comprises assaying said segregating population for increased *Colletotrichum trifolii* race 5 resistance.

5. The method of claim 1, wherein a sample of seed comprising said *Colletotrichum trifolii* race 5 resistance allele was deposited under ATCC Accession No. PTA-124210 or under ATCC Accession No. PTA-125043.

6. A method of identifying an alfalfa plant that comprises a genotype associated with resistance to *Colletotrichum trifolii* race 5 comprising:

a) detecting in an alfalfa plant the presence of a genomic region comprising an allele that confers resistance to *Colletotrichum trifolii* race 5, wherein said genomic region is flanked by marker locus FG2208 (SEQ ID NO: 1) and marker locus FG27271 (SEQ ID NO: 7) on chromosome 4, and wherein said resistance allele comprises a marker selected from the group consisting of FG2208 (SEQ ID NO: 1), FG2218 (SEQ ID NO: 2), FG27062 (SEQ ID NO: 3), FG2226 (SEQ ID NO: 4), FG27232 (SEQ ID NO: 5), FG27251 (SEQ ID NO: 6, and FG27271 (SEQ ID NO: 7);

b) selecting said alfalfa plant from the population of alfalfa plants based on the presence of said genomic region; and c) crossing the selected alfalfa plant with a second alfalfa plant lacking said genomic region to obtain at least a first progeny plant comprising said genomic region.

7. The method of claim 6, wherein detecting comprises detecting a polymorphism at a locus selected from the group consisting of FG2208 (SEQ ID NO: 1), FG2218 (SEQ ID NO: 2), FG27062 (SEQ ID NO: 3), FG2226 (SEQ ID NO: 4), FG27232 (SEQ ID NO: 5, FG27251 (SEQ ID NO: 6), and FG27271 (SEQ ID NO: 7).

* * * * *

SEQUENCE LISTING

```
Sequence total quantity: 7
SEQ ID NO: 1            moltype = DNA  length = 1002
FEATURE                 Location/Qualifiers
source                  1..1002
                        mol_type = genomic DNA
                        organism = Medicago sativa
SEQUENCE: 1
tgaggcttca cgatagatca ggtccataga gggctataaa taccaccctt gagagctttc  60
tcaagacata actaatataa gactaaactc taatatcgat tattgtactt cagcaagtac  120
aagatgatat gaaagataga ttataaatct ttaggattat aaatctctct cttaaatttt  180
ttttaacttt taacattctt aggattggat taaaggattt aaactttagg atttttagtt  240
aagttaaaag agactcaaat catctatgct ttttgctaga ttgagaatta attacaataa  300
aaaatgtgga atgaaataga acttaccaaa tagaaagaga atcaagagcc aattcaggat  360
gaggaagtaa cccagcaagc aaaaccaaga tttgaaagta ccaagtctct aaacacaaca  420
tcacagctga agcagctgac aatttaaaaa actctggcaa ccctgaaaat gcttgaaaac  480
taaacccttt ccaagtatgc ktacatttct cactcttcac aatataaaca aattgtgcaa  540
tcacaattat ccaccaagaa atactcaaaa ccaatgaagc acctaataaa ccaagcccaa  600
tttggtagat aacaacataa cttaacacaa ggtgaataac caatgttgct gctgatatgt  660
atgcacttgg tgctactatg ctttgtgctt gaagaaattt ttggattgga aagtttatag  720
cataggcaaa tatttgtggg attaaaccaa agacaaaaag ggatgctgct gatgcaattt  780
ttggtgattc tcctagaaat attaaaattg gttcggagaa tatgtatatt attgttaaaa  840
ttaaaccggc tattgtgaga agcactgttg atctttgcaa atatatgcct aacatttcat  900
atttttttgc tccaaatgct tgtccacata gtgtctcaac agcactcccc atgcccaact  960
gttcatcata aacatcacca attattcaaa aaaaaaatat ta                     1002

SEQ ID NO: 2            moltype = DNA  length = 1002
FEATURE                 Location/Qualifiers
source                  1..1002
                        mol_type = genomic DNA
                        organism = Medicago sativa
SEQUENCE: 2
aaggtactgc tataaatggt accttgtgat ccaactgatt catcaatgca aaaatccaac  60
ggcgatgaac attaatacac aaacaaggac aagcataagc atcagtacta atggaaatga  120
taaaatagta gtttcatgat aaatcaaagg gaacatagga ataccaacct tgaagagaaa  180
aatccttcaa gcttatatgg caaagatcat agatattctt ggtgacattt gctttctgca  240
acttctcccc aagtgataca gcacatttca aggcttgtag attggtcaca aagctttgtc  300
cttgcaaata ggagacataa tttttggttg ctttgcagca agatgtttga tttcttatct  360
gatttccaca ttcttttgca attcttgaga tattcggaaa aaccaacggg cagactgagt  420
aaatttatta taataacatt gaacataaac atgtcagatg tatgctacta tgatacatat  480
ttcaataaat tagccaaaag wtcaataatc aaacatgatg tatgatattg ttattgtatt  540
tttttctcc ttgctcacct ttgtttaggt tgcaatttga aagtcctcta aaaacactat  600
ttgctgctga tgagttgagt tttccggcca gccaacgtag aactatgttc ttacagtcat  660
taaccagagc cgtctttcga ggcaaactat ggtttccatt tgaattagac atgtcattta  720
aggaaatttt tctagcagca tagtttatag cattttggca tacttgatca caacattcat  780
ttacaggatc aatttttcta caagccgtta gaagtctgga agtgtctaca atgctctcaa  840
attcgtcgac aaacgcaaca ggacacgagc cttcagtgag atttgatgaa tggattgaac  900
atatattgtt taggtcttca gttgctcctt gactaacaag aaccttgtga acatcagaga  960
ggcagtgctt agcatgagtt gtgttcaaag ctaacactcc ag                     1002

SEQ ID NO: 3            moltype = DNA  length = 1003
FEATURE                 Location/Qualifiers
source                  1..1003
                        mol_type = genomic DNA
                        organism = Medicago sativa
SEQUENCE: 3
tgcgattctg attatgaagg tatatttgct gcctttattc atgtgtttga agtcttgtga  60
tgatttatct atttaagatg ttatattgcg agtgttatct agtttatcac aaaggacatg  120
atactgatgt ttctgaaatg tttgttgtct taaacttgag gaaatgtttg tgatgtggga  180
gtttgtttat gattctagtt aatttgtgat tggactttga atgaggagta aaatttactt  240
ggataacatt ttcttttctg ttaagatgaa aaattggaac ccttttatac tgcaaattta  300
```

```
gtgataaatt tcattctggt gacatagctg aaagcttctc tttgaaaaac tttaatgcag    360
ctgaagagat tggtggacag ctcccctttg acttgaatcg agatccgact ataatcatta    420
gtgattctga tggagaagat aatacttctg attcatctga ctttagcggg ccttcatcta    480
aacgagaaa  gacacggtcc araaagagag gtagtaaatc caagatagaa tctgcagacc    540
tgagtggtgt agagagtgcg ctggagttcg acctgagtgt tgtagagaga gcgctggagt    600
tcgatcaaag ttgtgtagag agagcgctgc agttcgacct gagtggtgta gagagagcgc    660
tgctggagtt tgatgatgag ttatttccaa tggtttctgc tgaagaggct ccatttgatt    720
tacctttacc taagctgcca aggaagaaaa aagcaaagaa gacaaaaaag ggagatccta    780
aaccagtgtt gttatggcat gcttggaaac aggaacatga gaagtggatc gatcagaatt    840
tgctggaaga tgttaccctc gatcagagtg aagtgatgaa tgagacggcc gaggcatcgt    900
cagatctgat tgttccgttg ctgaggtacc aaagggaatg gttagcatgg gctttgaagc    960
aggaggaatc tgtaaccaga ggaggaatcc ttgctgatga aat                     1003

SEQ ID NO: 4           moltype = DNA   length = 1001
FEATURE                Location/Qualifiers
source                 1..1001
                       mol_type = genomic DNA
                       organism = Medicago sativa
SEQUENCE: 4
ttcattttg  gaggatattc atatctaaat ctttatactt aatattgtta caactttgca     60
aacatttgat ccgtcttccg aagcgttttc tctgtttgaa tgatttaatt agaagttctg    120
tttttacact attgcattgt tcactttttt tttatcatta tttcattgtt tactgattat    180
attcgctata cctgtgctct tttgcagctc ctcaaagta tgttcaaact gctcccacag     240
ttctgttagg cattttgtt  ggtggaacaa ggtaagtct  gcagttttg  gtcttttttg    300
gttgggttct ccatattaga gagaatgaga gaagagttgt tccttgtaat tttatacaca    360
agatgtttta gctgacgttt ttttaaccat ttgtttaatc ttgattagaa tattgccaca    420
ccaattcaat catccggcta tggtgatgat gggaaaagag ctatgatttt gctcaaaaac    480
aaactttta  agagcatagt mttaaggcga actaaaatag gcagggctgc tgatcttgca    540
cttccgccta ggatcgtgag ttcttgttcc ccgatgacta agtatggatt tcttcatatg    600
aagagactac aaatttattt ctacaacatt tcttcttgca ggtttcattg aggagggata    660
gcctggatat aaaagagcaa gactattatg aatcactata caatgaaagt caggcacaat    720
ttaatacgta tgtcaaattc cttatcttac tgcctaaaat gtggtaaaat gtagttctgt    780
atttgaagaa attgaaatgt gtttgacatg aatgacatta tatttatttg gtggggttgg    840
atttgtggat caaatcacta aactgttagt gaggggaata tgagggtagc aaggcgaggg    900
aggaaatcat tttattgttg attgttggtt aggagagtat tctctctggt agtagcattc    960
ctctggttta tttccttca ttgtagagcc tttgtgctca a                       1001

SEQ ID NO: 5           moltype = DNA   length = 1002
FEATURE                Location/Qualifiers
source                 1..1002
                       mol_type = genomic DNA
                       organism = Medicago sativa
SEQUENCE: 5
cctttgttac agtttttggc tccagtatgt taatgttgta caatttttt agattttggg      60
gcacacattc tgatgttaag gcacagggat tgcaatatct gaaaaatgt gtcaaatctg    120
aatccataat ttttattga aggtggacac ttgtaaggac cgtattgcat ctgcacttga    180
aacacttaga ccaacaactt cgtgggagag aactccggca gcaggtcaag gaatggatgg    240
tgttctgcta ggtgggcgcg gttttggggc ggcaatggaa tctctctgta gttatcttgg    300
atctgaatat ggaaacactt tgcattagg  tttgtatgat tatccacaaa tcttaccata    360
tatgattttt gttaacatgc ttcttaatg  tttaatcttg cctcaaagtt tcaattagcc    420
attatttcta ttgaatactg cagctagagt ctttgcattc ttgtctggtc ctcctgatta    480
tggagctgga caattggaca cragacgata tggtgagcaa tatgcaagca aaagggagga    540
tgctgaccgt gctttactcc cggagcagac accatttat  aaagatctgg tatttaactt    600
attgttatta atactgctat ttcccatttc cttgaagtta agaactgac  atgtgtttca    660
caggctgctg ttgctgttca agcaggtgta tgtgttgaca tctttgccgt aacaaatgag    720
tacactgatt tggcatccct aaaatttctg agtattgaaa gtgggggctc ttattttttt    780
tatacaagta ccgaggattc aactttgcct caggacatgt aagtcccatc tggtaacttt    840
aatatgtcta gacatgtttt actggtaaaa ccattttaat tgttatgata tgtatcaatg    900
ggagacagtt atccaatatt tgctgattgg atgtgtatcc atgtcttcaa tacaatctca    960
gcttgaggcg gtattatacc attttctctt aaatcccatt gg                      1002

SEQ ID NO: 6           moltype = DNA   length = 1002
FEATURE                Location/Qualifiers
source                 1..1002
                       mol_type = genomic DNA
                       organism = Medicago sativa
SEQUENCE: 6
gaaaaatgt  gtcaaatctg aatccataat ttttattga aggtggacac ttgtaaggac     60
cgtattgcat ctgcacttga aacacttaga ccaacaactt cgtgggagag aactccggca    120
gcaggtcaag gaatggatgg tgttctgcta ggtgggcgcg gttttggggc ggcaatggaa    180
tctctctgta gttatcttgg atctgaatat ggaaacactt tgcattagg  tttgtatgat    240
tatccacaaa tcttaccata tatgattttt gttaacatgc ttcttaatg  tttaatcttg    300
cctcaaagtt tcaattagcc attatttcta ttgaatactg cagctagagt ctttgcattc    360
ttgtctggtc ctcctgatta tggagctgga caattggaca cragacgata tggtgagcaa    420
tatgcaagca aaagggagga tgctgaccgt gctttactcc cggagcagac accatttat    480
aaagatctgg tatttaactt aytgttatta atactgctat ttcccatttc cttgaagtta    540
agaactgac  atgtgtttca caggctgctg ttgctgttca agcaggtgta tgtgttgaca    600
tctttgccgt aacaaatgag tacactgatt tggcatccct aaaatttctg agtattgaaa    660
gtgggggctc ttattttttt tatacaagta ccgaggattc aactttgcct caggacatgt    720
```

-continued

```
aagtcccatc tggtaacttt aatatgtcta gacatgtttt actggtaaaa ccattttaat  780
tgttatgata tgtatcaatg ggagacagtt atccaatatt tgctgattgg atgtgtatcc  840
atgtcttcaa tacaatctca gcttgaggcg gtattatacc attttctctt aaatccccatt  900
ggatattttt gtactaacca tatgaaattg aatgcttatt atcgtatata tacacatttt  960
aaagtaatca agtccaatta aattgaccac ttatgctttt ta                   1002

SEQ ID NO: 7           moltype = DNA  length = 1003
FEATURE                Location/Qualifiers
source                 1..1003
                       mol_type = genomic DNA
                       organism = Medicago sativa
SEQUENCE: 7
agaacatgtt atatcatata tgcatatgta ttacatagat ttataaaaag ataactaata  60
aaaaagatct gatatgctag acactaaatg cctgaatgac tcatagtgtt atgacatgat  120
aacttaggaa catattccag ttggaaaaaa cataacacac taatatcact accatgtata  180
gagttagact cagagaaact aagagaaatt agggatgtta aactcagaga gaccaagaga  240
aatgagggtc aaaactgtgt ccctcttcat tctgatttct cgtataaata caatgtattt  300
acaagctgtc aagttgactt tcaacccact aaattagcta aactgacata tgtatattta  360
cagctaatta tgctaattga aagaatgatt ttatgactat tacaaataaa tgtgcaatct  420
tatagaattt gatttgccat taattccatt gacatatagg caatgtgaat aatttagcag  480
cttatggcat aaaactataa twcccaaatg aacaaggcat agttttgaaa actcaccact  540
acctccaaaa tcaggagaac caatgttcag tcgcttccct acacgagtca aaaccttgcg  600
ttctttctgc ttttttgaag gagggcgccc atatttgctg cattaacaac caggtatgat  660
gacagttgaa aacagaagta gaaaggataa atcatacaaa taaaatcatc atacgtttta  720
ttcttatcat taggacttgt ttcctgaact ggcttcagta taggtacatt ctcagacttc  780
tccctcccta acggaaggcc tggtcttatt gacgataaat tccttccagg tcttccttgt  840
ctctgcatac catctcctga ttcatctctt ggcattttat tcttcctcat ttgtaacata  900
ggagatccat ccctatcagc agccaaagca aagtcactgg cattcacccc tttctctttt  960
attttgtttt cgccagcacc agattcttca ctttcagata atc                  1003
```